United States Patent [19]

Alais

[11] Patent Number: 4,481,823

[45] Date of Patent: Nov. 13, 1984

[54] ULTRASONIC PROBING DEVICES

[75] Inventor: Pierre Alais, Dampierre, France

[73] Assignee: Centre National de la Recherche Scientific, Paris, France

[21] Appl. No.: 394,913

[22] PCT Filed: Oct. 26, 1981

[86] PCT No.: PCT/FR81/00139

§ 371 Date: Jun. 22, 1982

§ 102(e) Date: Jun. 22, 1982

[30] Foreign Application Priority Data

Oct. 24, 1980 [FR] France ............................... 80 22880

[51] Int. Cl.³ ........................................... G01N 29/00
[52] U.S. Cl. ....................................... 73/626; 73/625; 73/628; 307/262; 307/320
[58] Field of Search .................... 73/625, 626, 628; 307/320, 262; 328/55

[56] References Cited

U.S. PATENT DOCUMENTS

| | | | |
|---|---|---|---|
| 3,202,769 | 8/1965 | Coleman, Jr. | 328/55 |
| 3,882,431 | 5/1975 | Hopwood et al. | 307/320 |
| 4,005,382 | 1/1977 | Beaver | 73/626 |
| 4,084,582 | 4/1978 | Nigam | 73/626 |
| 4,116,229 | 9/1978 | Pering | 73/626 |
| 4,119,938 | 10/1978 | Alais | 73/626 |
| 4,140,022 | 2/1979 | Maslak | 73/626 |
| 4,257,271 | 3/1981 | Glenn | 73/626 |
| 4,330,875 | 5/1982 | Tachita et al. | 73/626 |

*Primary Examiner*—Howard A. Birmiel
*Attorney, Agent, or Firm*—Larson and Taylor

[57] ABSTRACT

The device comprises n spaced transducers associated with a generator through phase-shift means. These means are formed by members (66) for supplying, on different channels and from the same pulse of the generator, pulses with different time delays. Amplifiers are each associated with a transducer and are controlled from the pulse appearing on the appropriate channel selected by storage means. A receiver (62) associated with the transducers (12) comprises a single delay line with multiple taps closed upstream across a matched impedance and forming phase-shift means at reception.

9 Claims, 9 Drawing Figures

ULTRASONIC PROBING DEVICES

The present invention relates to ultrasonic probing for exploring a part or an organ to be analysed, more especially although not exclusively, in depth, i.e. by echography B.

There is described in French Pat. No. 2 472 753 and corresponding U.S. Pat. No. 4,351,038, an ultrasonic sonic probing device of the type comprising n elementary transducers spaced apart at even intervals, a generator associated with the transducers through members adapted to supply, on different channels, from the same pulse of the generator, pulses delayed by time $\tau$ and multiples of $\tau$, means for storing the distribution over n successive elementary transducers of the delays corresponding to focusing at a given distance from the line, means for connecting a group of n transducers to the phase-shift means and to the generator in accordance with the distribution selected by the storage means, and a receiver associated with the transducers.

The device described by way of example in French Pat. No. 2 472 753 uses, for reception, switching means which comprise a multiplexer (which is also generally used for emission) associated with each transducer and connected, by a common bus line having a channels in which are inserted phase-shift means, to a summing circuit for summing the reception signals, each multiplexer comprising a multibit control input connected to a respective stage of a phase-shift register associated with a clock for moving said stored distribution along the register. These phase-shift means are formed by several separate phase-shifters or delay lines.

The a phase shifts may be spaced evenly apart, but in some cases it is more advantageous to provide different intervals, for example so as to take into account the variation of the slope of the curve representative of the phase as a function of the distance to the centre of the group of n transducers.

The present invention aims at providing an ultrasonic probing device of the above-defined kind, which is simple but allows however fine sampling of the phase or of the delay, focusing without a secondary lobe of a prohibitive level and continuous dynamic cocusing (also called tracking focusing) and not simply by discrete steps as in the case of the embodiment described in French Pat. No. 2 742 753.

To this end, the invention proposes more especially a device of the above-defined kind, in which the receiver associated with the transducers comprises a single delay line having multiple taps, closed upstream across an iterative impedance formed of progressively variable delay cells and in which the transducers are connected to said taps through voltage-current amplifiers.

The use of the same multitap delay line for emission and reception is known per se see French Pat. No. 1 163 092, but using an arrangement which only allows the delays to be varied by switching. The use of a variable-delay line for each transducer for focusing at reception is disclosed in the French Pat. No. 1 163 092 but in a form which cannot be implemented in practice.

The delay line may be formed of identical LC cells connected together, each comprising an adjustable-impedance element. This adjustable impedance element is formed for example by a VARICAP diode. The diodes of all the cells then receive the same control voltage. So that the delay line may remain closed in all cases on its iterative impedance, the line may be looped upstream across a series of LC cells each comprising a VARICAP diode. All the diodes are then biased by a line to which there is applied, at the upstream end, a fixed voltage and, at the downstream end, the voltage for controlling the VARICAP diodes. A resistance bridge is placed across the cells forming the iterative impedance so as to ensure the correct spacing out of the voltages over the VARICAP diodes and the iterative impedance.

The focusing distance may be controlled manually by operating a control voltage generator: thus, a medium may be examined in depth by focusing, at reception, on the interesting zone. There may also be provided in the device a control-voltage generator which, during a sequence of successive shots of a given number, modifies the focusing distance each time so as to provide exploration in depth which may be displayed as a whole on a visualization device, such as a tube with cathode-ray screen.

The invention will be better understood from reading the following description of devices which form particular embodiments thereof, given by way of nonlimiting examples. The description refers to the accompanying drawings, in which:

FIG. 1 is a diagram showing the distribution of the delays to be provided over transducers spaced apart at even intervals in a direction plotted along x-axis and identified as Ox so as to provide focusing at a predetermined distance from the tranducers;

FIG. 1a, similar to FIG. 1, shows the distribution of the constant delays to be provided so as to obtain the same result;

Figure 3:
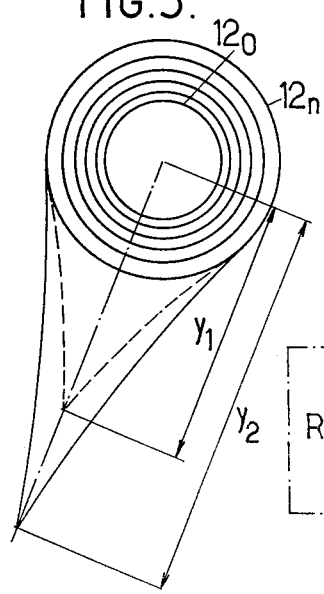
FIG. 3 is a simplified diagram of a circuit for implementing the invention without electronic scanning.
Figure 8:
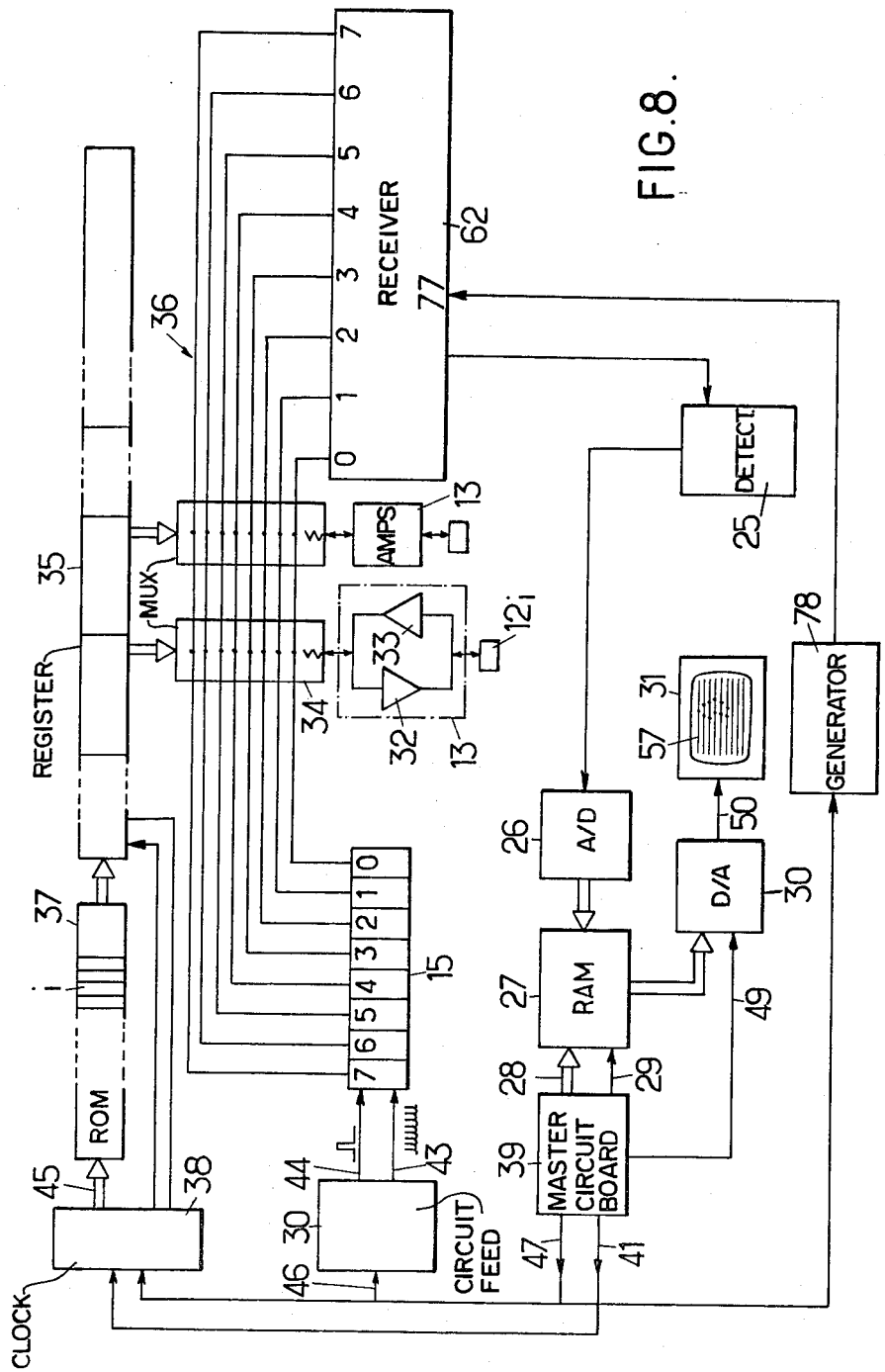

FIG. 8, similar to FIG. 3, is a diagram showing an electronic scanning device.

Figure 1:
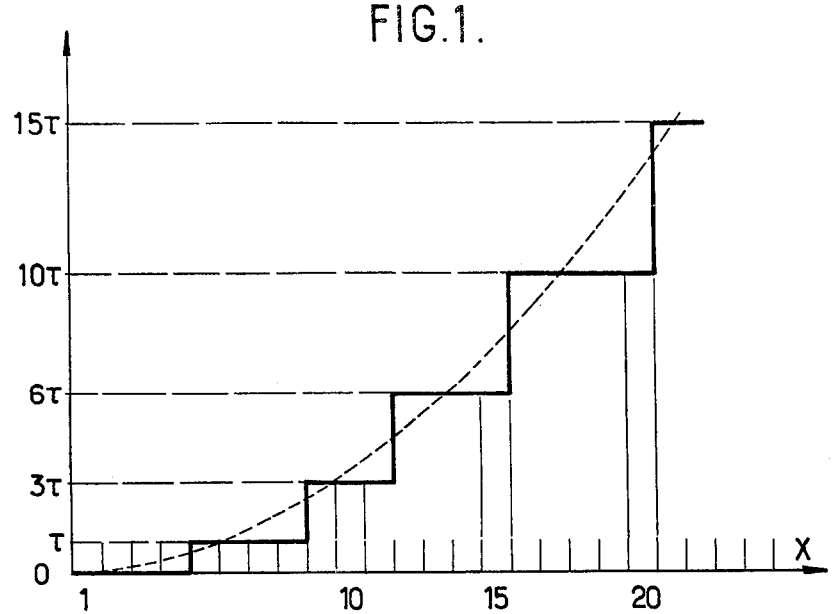

As French Pat. No. 2 472 753 already mentions, focusing may be achieved at transmission or reception at right angles to a group of n transducers spaced apart in a direction Ox at a distance y from the right-hand segment over which the n elementary transducers are distributed, by using a phase distribution between the transducers which simulates the phase-shift variation $\Phi$ as a function of abscissa x from center O. The broken-line curve of FIG. 1 shows the theoretical distribution of the phase to be obtained. The theoretical relationship may be approximated by sampling the phase at a levels, a being a whole number, and by allocating to each of the n transducers the modulo $2\pi$ phase the closest to the value of the phase attained by the law of variation of $\Phi$ as a function of x.

However, so as to reduce the side lobes of the transmission or reception diagram, it is more advantageous to assign to the elementary transducers delays spaced apart so as to simulate the law of variation of $\Phi$ as a function of x. Since this law is itself parabolic, a first solution consists in carrying out sampling at several delay levels, the successive delays being distributed according to a parabolic law. If the elementary transducers are then regularly spaced apart, each of the delays will be applied to an equal number of transducers, which may be reduced moreover to a single transducer. FIG. 1 shows with a continuous line such a distribution of the successive delays, each time applied to four elementary transducers.

Figure 1A:
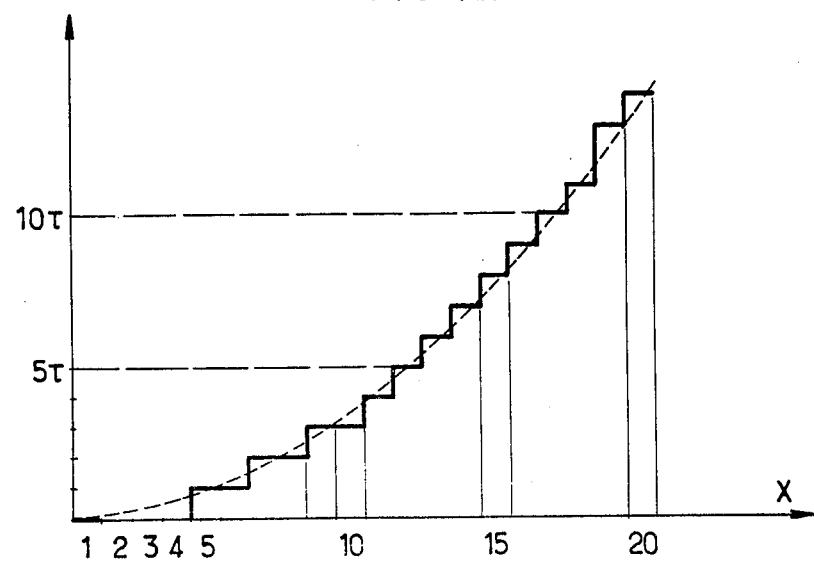

In the variation shown in FIG. 1a, the delays are on the contrary spaced apart at constant intervals, but the number of transducers is not the same for all the delays.

Figure 2:
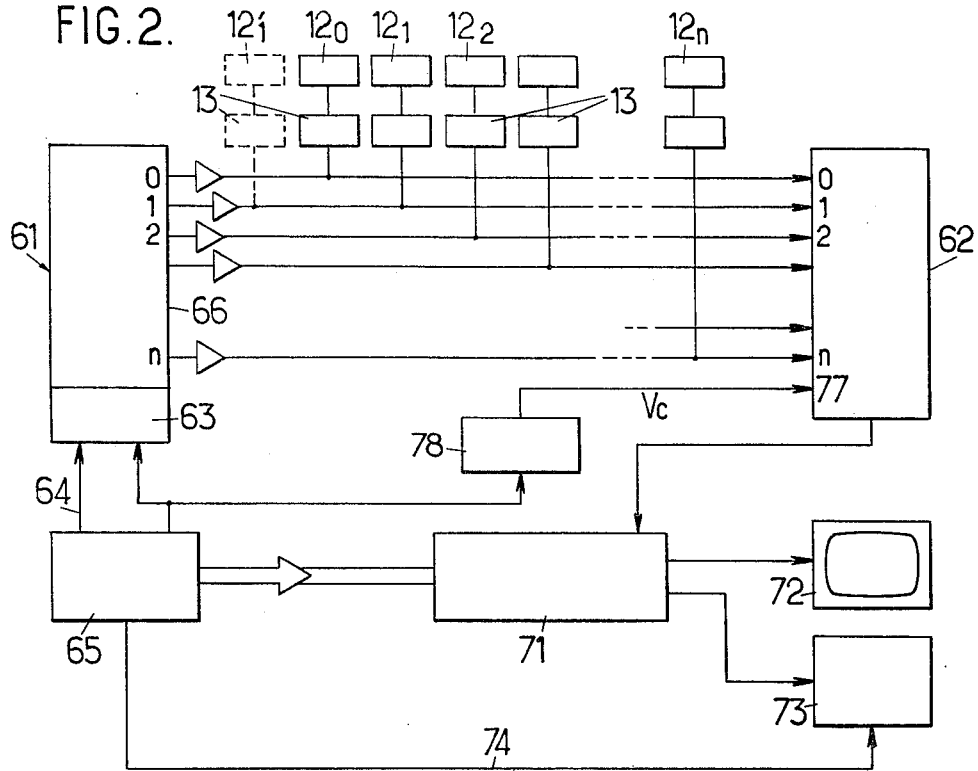
FIG. 2 shows a possible arrangement of n elementary transducers, for implementing the invention.

The electronic circuit shown schematically in FIG. 2 is intended to provide an approximation of the Fresnel curve by use of delays spaced apart according to a parabolic law. This simulation is the one shown in FIG. 1, except that to each elementary transducer there is assigned a particular delay.

The circuit shown in FIG. 2 is associated with a system of n transducers $12_0, 12_1 \ldots, 12_n$ excitable by pulses. The elementary transducers may be annular in shape, as shown in FIG. 3. They may also be spaced apart along a linear strip, as in the case shown in FIG. 2 of French Pat. No. 2 292 978, in which case the same delay will be assigned to two transducers such as $12_1$ and $12'_1$ placed symmetrically with respect to a central transducer $12_0$.

The elementary transducers are connected, through respective excitation and amplification circuits 13 which will be described below, to the n channels of a bus line 60 which connects a generator 61 to a receiver 62. The generator comprises a clock 63 having a gate input 64 connected to a master circuit board or card 65, which may incorporate a microprocessor. Generator 61 also comprises a shift register 66 whose n outputs are connected to the channels of the bus line 60 through shaping amplifiers. Clock 63 is provided so as to supply, for each complete operating sequence, in response to the gate signal which is applied thereto at input 64, a control signal intended to transit in register 66, and thereafter short pulses for causing the control signal to circulate in register 66. The positions of register 66 which are connected to channels n, ..., 2, 1, 0 of register 66 are chosen so as to correspond to delays 0, $\tau$, 3 $\tau$, 6 $\tau$, so on so as to correspond to the distribution of FIG. 1 and so to provide focusing at a predetermined distance, which will be for example the distance $y_1$ of FIG. 3. This parabolic distribution may be replaced by a linear distribution 0, $\tau$, and so on.

Figure 4:
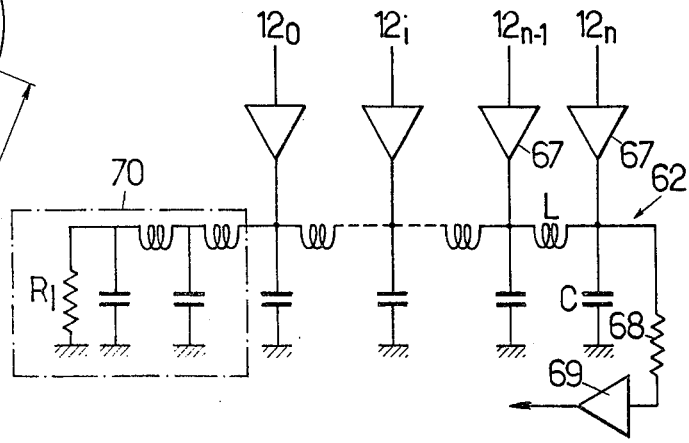
FIG. 4 shows a particular embodiment of the delay line usable in the circuit of FIG. 3.

Receiver 63 uses a multitap single-delay line. This receiver may have the general construction shown in FIG. 4. This receiver comprises a delay line formed of cells, all identical, of the LC type. Each of the channels of bus line 60 drives the line through a voltage-current amplifier 67. A single cell, supplying the elementary delay $\tau$, is inserted between the connection points of the amplifiers from channels of order n and n−1. The number of cells then increases linearly and thus there is in fact achieved parabolic growth, since the derivative of the function $x^2$ is equal to 2 x. The delay line then drives, through a resistor 68, a current-voltage amplifier 69 which forms the output member of receiver 62.

The delay line must be connected upstream to an impedance which constitutes a matched termination, so that the signals injected at each tapping of an elementary transducer and propagating upstream are not reflected at this upstream end. This matching is achieved by looping, i.e., closing, the line across a cell 70 comprising LC networks and a resistor $R_I$ whose value is:

$$R_I = \sqrt{L/C}$$

On the other hand, it is not necessary to provide such matching downstream of the line, since the possible reflections cannot cause an error on the received signal.

The output signal of receiver 62 is applied to a complex circuit 71 which may comprise logarithmic compression, detection, digitization and/or storage circuits. A display device, comprising typically a tube with cathode-ray screen 72, allows the results to be displayed. When circuit 71 must effect memorization, the addresses will be fed thereto from card 65, comprising possibly a microprocessor.

The display may be completed by means of an oscilloscope 73 which receives signals at the shot-recurrence frequency from the master card 65 through a line 74.

Figure 5:
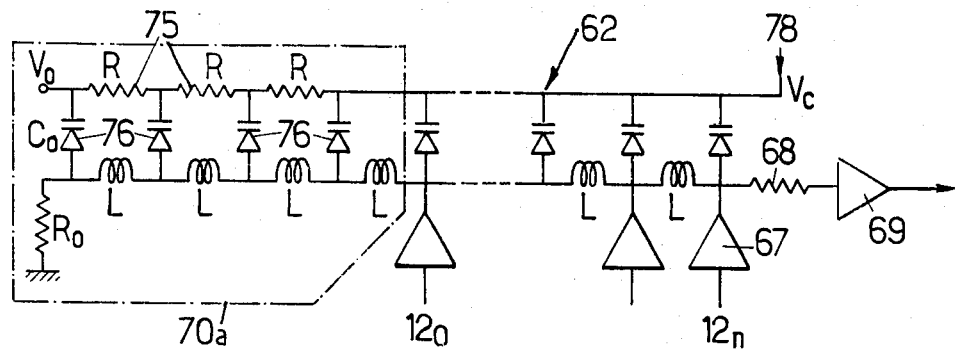
FIG. 5 shows a possible construction of the delay line of FIG. 4, for providing dynamic focusing at reception.

Tracking focusing may be obtained, by means of the device which has just been described, by using a delay line 62 whose cells have characteristics which may be progressively and continuously modified by means of an electronic control having the construction shown in FIG. 5.

In the embodiment shown in FIG. 5, this result is attained by using capacities which are not of a constant value, but of a value modifiable for all the capacities at one and the same time. For that, these capacities may be formed by voltage control elements. In particular, they may be "VARICAP" diodes whose capacity depends on a control voltage $V_c$. Some commercially available VARICAP diodes have a capacity which varies in a ratio from 1 to 10, which causes a relative variation of the delay $\tau$ in a ratio of 1 to 3 approximately. It is then necessary to place voltage-current amplifiers, forming current injectors, between the transducers and the taps of the line, so as to avoid the modifications of the characteristics of the line which charging thereof would cause.

In the embodiment shown in FIG. 5, the inductance line L is biased to a constant DC voltage through a resistor $R_0$. The diodes are placed between the line brought up to the control voltage $V_c$ and the constant reference voltage.

The delay line must be further looped across its iterative impedance. Now this latter is variable as a function of the variable value of the capacities: it must then vary as a function of $V_c$.

The problem is resolved in a simple way, in the delay line of FIG. 5, by providing an upstream matching branch 70a comprising a bridge of resistors 75 of value R ensuring a linear voltage variation of value $V_c$ from the control voltage to the fixed value $V_0$. To each resistor 75 is assigned a cell comprising an inductance L and a "VARICAP" diode 76. It can be established experimentally that the progressive development of the characteristics of the upstream matching branch 70a from the variable characteristics imposed by $V_c$ up to the constant characteristic imposed by $V_0$ (and which gives to the last "VARICAP" diode a capacity $C_0$) allows suitable matching across resistor $R_0 = \sqrt{L/C_0}$ to be achieved not only when $V_c = V_0$, but also for a large range of variation.

With this arrangement, the elementary delay may be varied in a proportion typically from 1 to 3, which allows tracking focusing in a zone between distance $y_1$ and distance $y_2$ (FIG. 3) such that $y_2/y_1 = 3$. In medical tomography, a useful zone may for example be adopted from $y_2 = 30$ mm to $y_1 = 100$ mm.

In order that this tracking focusing may be carried out automatically, the device of FIG. 2 comprises a control generator 76 whose control input is connected to the master card 65. During a complete operating sequence, the master card 65 then supplies to generator 78 successive pulses which result in a voltage $V_c$ of increasing value being supplied to an analog input 77 of receiver 62.

Instead of using linearly increasing delays, i.e. a distribution of the kind shown in FIG. 1, constant delays may be used but by assigning a variable number of transducers to each delay, which may be done in a simple way by using a bus line.

Figure 6:
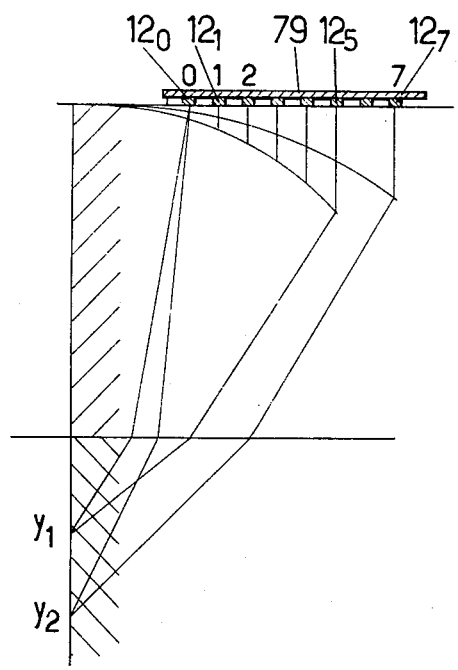
FIG. 6 is a diagram illustrating the principle of dynamic focusing with nondestructive testing.
Figure 7:
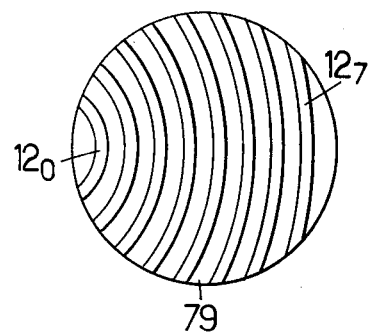
FIG. 7 shows a possible distribution of the elementary transducers for nondestructive testing.

The device shown in FIG. 2 is susceptible of numerous applications, among which may be mentioned the nondestructive testing of parts. FIGS. 6 and 7 show by way of example the application of the device of FIG. 2 to nondestructive testing, by means of an off-center probe 79 comprising several elementary transducers in the form of ring fragments. Scanning may then take place from a distance $y_2$ to a distance $y_1$ along a firing axis. So as to avoid too high an opening when focusing is at a small distance, it is possible to reduce the number of elementary transducers which are then used, for example from 7 to 5 (FIG. 6). The control voltage may be controlled manually or automatically.

The device shown schematically in FIG. 2 allows tracking focusing, but is not adapted to carry out electronic scanning. But the device of the invention may comprise the circuitry required for electronic scanning and at the same time allow continuous tracking scanning rather than scanning by discrete steps. The device may then have the construction shown schematically in FIG. 8, where the parts already described in French Pat. No. 2 474 753 bear the same reference number.

The circuit will only be briefly described since reference may be made, for complete understanding, to French Pat. No. 2 474 753. The electronic circuit shown schematically in FIG. 8, in which only a single elementary transducer $12_i$ and its associated amplifier-receiver circuit 13 is shown, is intended to provide an approximation of the Fresnel curve by using eight delays and, at reception, n elementary transducers with continuous dynamic focusing.

The circuit of FIG. 8 will have to cause excitation of the n transducers $12_i$ with a given delay distribution. So as to achieve the distribution shown in FIG. 1a, the circuit will apply for example the excitation signal with a maximum delay to the transducers or order 1, 2, 3, 4; it will cause a delay less than T/8 (T being the period) of the signal applied to the transducers of order 5 and 6 and so on.

The circuit shown in FIG. 8 is provided for association with a system of N transducers $12_1, \ldots, 12_i, \ldots, 12_N$, excitable by pulses. The excitation and amplification circuit 13 associated with each transducer $12_i$ comprises a nonlinear threshold amplifier 32 capable of delivering the high emission signal required from a logic control, looped by a protected linear amplifier 33 transferring the reception signals in the return direction and whose output is limited in amplitude so as to avoid any natural oscillation of the loop thus formed.

With circuit 13 of each transducer 12 are associated switching means which have now only weak signals to transit, typically of 5 volts at most at emission, of the order of 100 mV at reception. They may be simply constructed, for example from an analog multiplexer 34 having a channels. In the case shown where $a=8$, low-price C-MOS or complementary MOS multiplexers may be used, for example of type CD 4051, which may only transfer logic signals, whereas the amplitude of the voltage oscillation at the transducer, typically a ceramic transducer, may exceed 100 V at emission.

All the multiplexers 34 are disposed on the same bus line 36 having a channels (eight channels in the embodiment illustrated) and are controlled by a shift register 35. The control by the register must allow each transducer to be connected to any one of the eight channels, marked 0, 1, . . . , 7 in FIG. 8, of bus line 36 or must allow this transducer to be isolated. Accordingly, each multiplexer 34 must be controlled by a word of four bits, three for selecting the channel, and one for isolating the transducer or connecting it.

With read-only memory (ROM) 37 is associated a clock 38 which sequentially transfers the four-bit words from ROM 37 into register 35. The transfer of the four bits of the same word takes place simultaneously on reception of a signal transmitted by the clock over four channels 45. Clock 38 drives at the same time the clock input H of register 35. As described already in French Patent of Addition No. 2 355 288 (corresponding to U.S. Pat. No. 4,117,466), the changeover from a configuration corresponding to transmission to a reception configuration may be effected in response to a clock pulse from a clock 38 which actuates at the same time RAM 37 through 45 and register channels 35. The changeover from one firing to the next firing line, staggered by a distance corresponding to the spacing of two transducers, takes place in a number of pulses of clock 38 equal to that required for all the shots at different focusing depths.

The "transmission" part of the circuit uses the fact that the phase advance is equivalent to a time advance, a phase difference of $2\pi/8$ corresponding to a time shaft equal to T/8, T being the period of the ultrasounds emitted.

This "transmission" part comprises a circuit board or card 30 having a clock with a gate input 46 and two outputs 43 and 44. Output 44 is provided so as to supply a control signal for transiting in a register 15 with eight binary positions, each associated with one of the channels 0 to 7 of bus line 36. Card 30 is provided so as to supply at its output 43, in response to the gate signal applied to input 46, a sequence of eight short pulses, of the order of 1 microsecond for example, at a frequency equal to eight times the nominal frequency of the ultrasonic signals.

Clock 38 and circuit board 30 are connected to a master circuit board or card 39 which ensures sequencing of the whole of the operations. This card is provided so as to emit, at an output 41, a signal for controlling clock 38 at the beginning of each complete operating sequence. This signal will be called "frame synchronization". Card 39 further emits, at another output 47, a signal, which will be called "line synchronization", applied to clock 38 and the clock of board 30.

Receiver 62 of the circuit of FIG. 8 may be identical to the one shown in FIG. 5 and thus will not be described again.

The signal provided by receiver 62 then undergoes conventional logarithmic compression, detection and depth-gain correction processing, in a complex circuit of conventional type, denoted 25. Circuit 25 receives, at a control input 48, the line synchronization signal coming from master card 39. The output of circuit 25 is connected to an analog-digital converter 26 whose output, for example a four-bit output allowing quantification at sixteen levels, drives an addressable read-write digital memory 27, of a capacity sufficient to be able to store a complete image. This memory 27 is also provided with an input 28 for addressing by master card 39 and a write-order input 29. It will be generally formed from RAM memories whose read cycle may be addressed and controlled independently of the write cycle. In the case where N=160 transducers, memory 27 will then have a capacity of at least 2.5×160 four-bit words and will allow stored data to be read according to a line-frame standard for driving a conventional video monitor 31, with television scanning, or a video taperecorder for recording and filing views. The reading is permanently carried out by a circuit 30 comprising a digital-analog converter and a synchronizing circuit which receives the line and frame synchronizing signals from master card 39 at an input 49 and supplies a composite video signal at output 50.

I claim:

1. A device for focussing an ultrasonic image received by an array of elementary transducers distributed along a line, comprising:

a delay line having a plurality of serially connected electrically controllable delay cells each providing a predetermined time delay, and having one of its ends connected to a matched termination, taps provided between successive ones of said cells, a plurality of voltage-current amplifiers each connecting an individual one of said transducers to one of said taps in accordance with a connection pattern which provides focusing at a predetermined distance from said array amplifier means connected to the other of the ends of said delay line for summing the signals received from said transducers, and means for simultaneous and progressive control of all of said cells for modifying the time delays provided by said cells while maintaining the same ratios between the time delays provided by said cells.

2. A device according to claim 1, wherein said delay line is formed from LC cells and said taps are distributed along said line such that the delays between successive taps increase along said delay line according to a parabolic law, each tap being assigned to a group of said transducers and all groups comprising the same predetermined number of transducers.

3. A device for ultrasonic imaging, comprising:

n elementary transducers spaced apart intervals along a line, n being a predetermined integer, a generator for generating electrical pulses one at a time, delay means operatively connected to said generator to receive said pulses and for supplying a plurality of delayed pulses at equal time intervals responsive to each generator pulse, means for connecting said transducers to said delay means in accordance with a distribution providing focussing at a predetermined distance from said line, and a receiver associated with said transducers, wherein said receiver includes a single delay line comprising a plurality of serially arranged delay cells each controllable to provide a continuously variable time delay, controllable impedance means connected to one end of said delay line, means for simmultaneously controlling all of said cells and said impedance means such that said impedance means constitutes a matched termination for said line, a summing amplifier connected to the other end of said line, a plurality of delay taps distributed along said line between adjacent cells, and voltage-current amplifiers for connecting said taps to respective ones of said transducers according to a distribution which provides focusing at said predetermined distance.

4. A device according to claim 3, wherein the delay line is formed from identical LC cells, the taps being separated by an equal number of cells.

5. A device according to claim 4 with dynamic focussing, characterized in that the capacitance of each cell is formed by an element whose capacitance is adjustable by means of a control voltage.

6. A device according to claim 5, characterized in that said element is formed by a VARICAP diode.

7. A device according to claim 6, characterized in that the delay line is terminated at one end in a matched termination formed by LC cells, all of the cells being biassed by a line to one end of which is applied a fixed voltage and to the other end of which is applied the control voltage, a resistance bridge being placed across the cells forming the matched termination.

8. A device according to claim 5, 6 or 7, further comprising a control voltage generator whose output voltage is manually or automatically adjustable in response to the signals supplied by a master circuit board.

9. A device for focusing an ultrasonic image received by an array of elementary transducers, said device comprising a delay line having a plurality of serially connected electrically controllable delay cells each providing a predetermined time delay, and having one of its ends connected to a matched termination, taps provided between sucessive ones of said cells, a plurality of voltage-current amplifiers each connecting an individual one of said transducers to one of said taps in accordance with a connection pattern which provides focussing at predetermined distance from said array, amplifier means connected to the other end of said delay lines for summing the signals received from said transducers, and means for simultaneous and progressive control of all of said cells for modifying the time delays provided by said cells while maintaining the same ratio between the time delays provided by said cells, said array of elementary transducers comprising a plurality of elemetary transducers in the form of segments of rings of different radii and together forming an off-center probe.

* * * * *